United States Patent [19]

Cesar

[11] 3,944,204
[45] Mar. 16, 1976

[54] RADIOLOGICAL EXAMINATION TABLE

[75] Inventor: Jean Cesar, Milan, Italy

[73] Assignee: C.G.R. Generay S.p.A., Milan, Italy

[22] Filed: May 24, 1974

[21] Appl. No.: 473,063

[30] Foreign Application Priority Data
May 29, 1973 France .............................. 73.19497

[52] U.S. Cl. ...................... 269/323; 74/27; 108/20; 250/446
[51] Int. Cl.² ........................................ A61G 13/00
[58] Field of Search ............ 260/322, 323; 250/439, 250/442, 446, 449, 451; 108/1, 5, 9, 20, 147; 254/9 C, 122; 5/62, 63; 74/22, 25, 27

[56] References Cited
UNITED STATES PATENTS

| | | | |
|---|---|---|---|
| 2,774,079 | 12/1956 | Flatley | 108/147 UX |
| 3,013,281 | 12/1961 | Steiner | 5/62 |
| 3,131,301 | 4/1964 | Barrett et al. | 269/323 X |
| 3,462,772 | 8/1969 | Morrison | 108/147 X |
| 3,623,707 | 11/1971 | Klopp | 254/122 |

*Primary Examiner*—Roy Lake
*Assistant Examiner*—Neil Abrams
*Attorney, Agent, or Firm*—Edwin E. Greigg

[57] ABSTRACT

A radiological table includes a platform for supporting a patient. The table is equipped with a single supporting mechanism for effecting the desired different translational movements in the transverse direction and the vertical direction, and its rotation and about axes parallel to its longitudinal axis. The platform is suspended at each of its ends by a mechanism which includes two concentric cranks, each journalled at one of their respective extremities to a pivot integral with a carriage or slide block gliding in a slide fixed transversely at the end of the platform. The transverse position of each of the carriages in the slide is independently controlled by a pinion secured to a hollow shaft rotatably mounted on said pivot and engaging a chain whose two ends are fixedly secured to the opposite extremities of the slide. The mechanism is especially adapted for being used with tables associated with two x-ray tubes, the second x-ray tube having a beam which is perpendicular to that of the prncipal x-ray tube.'

3 Claims, 3 Drawing Figures

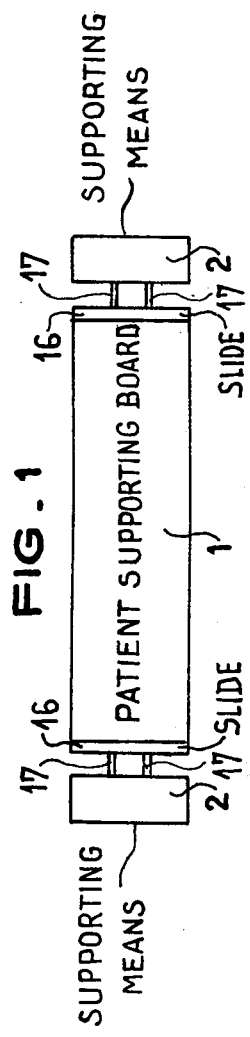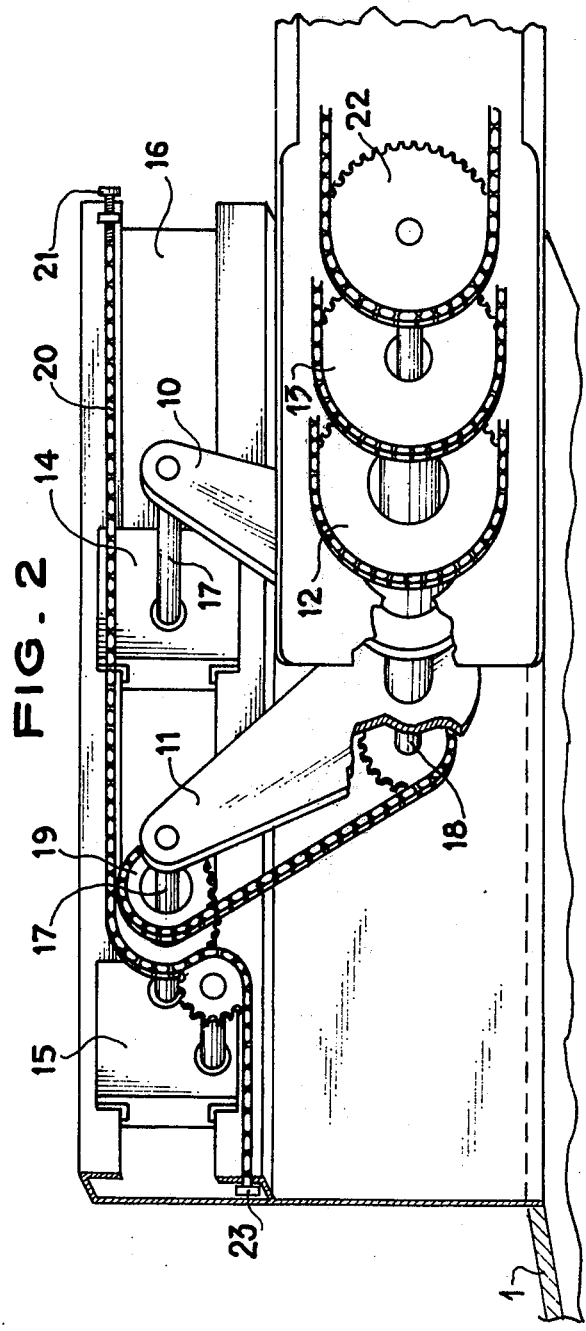

RADIOLOGICAL EXAMINATION TABLE

BACKGROUND OF THE INVENTION

This invention relates to a radiological examination table equipped with an apparatus for positioning and displacing a patient.

Present radiological examination tables make possible the shifting of the patient by means of different motions imparted to its patient-supporting platform in the longitudinal and lateral sense of the platform.

The presence of a motor means (motor, reduction gears and motion transfer members) makes it necessary that one or both ends of the patient-supporting platform, which are opaque to radiation, extend over a certain considerable length.

Futhermore, in cases of machines which have both longitudinal and lateral movement, an intermediate frame, which is subjected only to one of those two movements and which carries the driving assembly for the other movement, must be present.

This intermediate frame, aside from the manufacturing complications which it requires, has the distinct disadvantage, because of its thickness, of increasing the distance between the support plane of the patient and the film in the associated casssett or in a film handling device for bare film, when the latter is in the X-ray exposure field, in the case where there is a remotely controlled apparatus carrying the cassette receiver of the radiographic pictures below the patient-supporting platform.

Consequently, presently known tables have a certain number of disadvantages and are to some degree inconvenient. These tables could be advantageously improved, especially with respect to the possibilities of shifting or displacing the patient. Actually, especially with respect to longitudinal and lateral movements of a patient with respect to the examining assembly, it would be very desirable in the case of universal, remotely controlled tables, to be able to impart to the patient two other possibilities of motion, i.e. (1) a movement changing the height of the plane of the patient-supporting platform, and (2) an arcuate movement of the patient in the transverse sense.

In the case of a universal, remotely controlled apparatus equipped with a device for tomography, the desired height-changing movement permits the choice of the height of the layer of the patient's body (this layer being parallel to the plane of the film and traversed by the axis about which both the X-ray source and the film are moved in opposite directions) which is necessary for tomographic examination. It also readily permits use of techniques for optical magnification.

The arcuate movement is, from the medical point of view, very desirable because it permits changing the direction of force due to gravity with respect to the various organs in the patient's body. Consequently, it is made easy to study the movement and displacement of injected contrast materials, which may be either lighter or heavier than the region of the patient's body into which these materials have been injected.

Until the present time, this desirable arcuate movement has been achieved by a special mechanism which is independent of those which powered the other movements of the patent-supporting platform.

SUMMARY OF THE INVENTION

It is the principal object of the present invention to provide a radiological table equipped with an apparatus which permits imparting to the patient-supporting platform lateral movement, vertical movement and arcuate movement, and which is not subject to the above-mentioned disadvantages and inconveniences.

The foregoing object, as well as others which are to become clear from the text below, is achieved according to the present invention by providing a radiological table which includes a patient-supporting platform suspended at its two ends by a mechanism having two cranks whose rotational axis is essentially parallel to the longitudinal axis of the platform. The end of each the two cranks is pivoted in a carriage gliding in a slide fixed transversely at the end of the platform. A chain is provided whose two ends are respectively fixed to the opposite ends of the slide and engage a pinion mounted in concentric manner on the axis at the end of one crank on which one of the carriages is pivoted. The rotational movements of the toothed pinion and of each of the cranks are controlled in independent manner.

BRIEF DESCRIPTION OF THE DRAWING

FIG. 1 is a schematic plane top view of a patient-supporting platform which may be used as part of a radiologic examination table according to the present invention.

FIG. 2 is a partial exploded perspective view of one of the supporting mechanisms for the platform shown in FIG. 1, according to the present invention.

DETAILED DESCRIPTION OF THE PREFERRED EMBODIMENT

Figure 3:
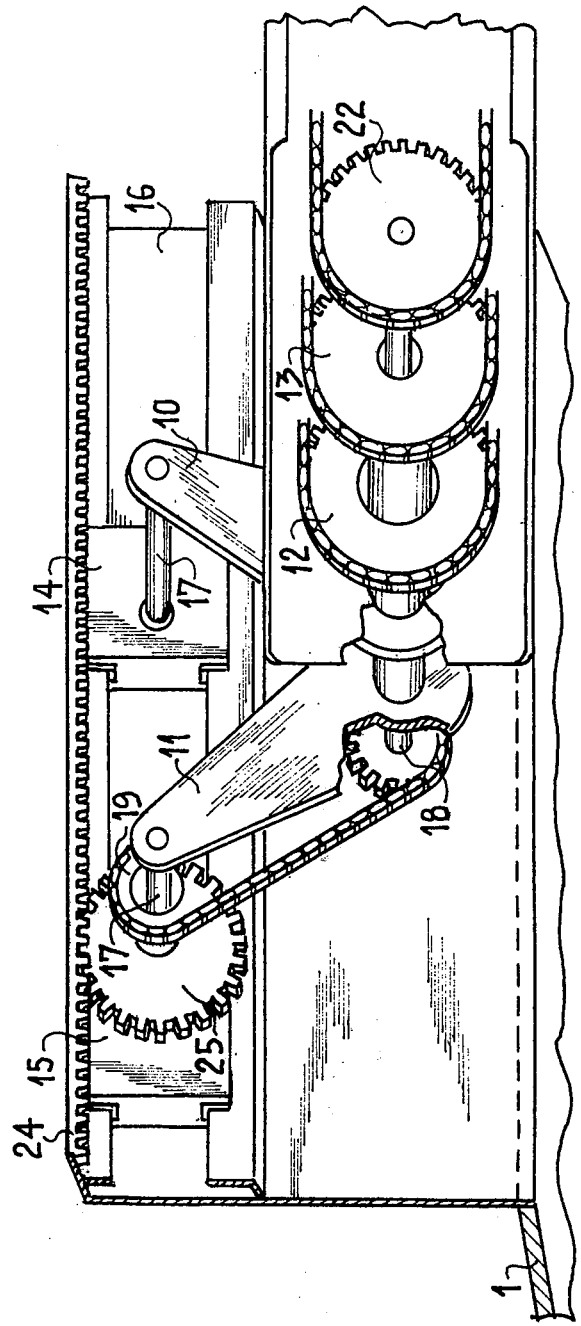
FIG. 3 shows a variant embodiment of the apparatus of FIG. 2 using a rack-and-pinion type drive.

Referring to FIG. 1, a patient-supporting platform 1 is supported at its two ends by two identical mechanisms 2 which are described in detail hereinafter.

As shown in FIG. 2, one of the mechanisms 2, which is repeated at the other end of the patient-supporting platform, includes two concentric cranks 10, 11 driven separately in rotation by chain sprocket wheels 12-13 whereto they are respectively connected by means of two hollow coaxial shafts. Each end of the cranks 10, 11 has a respective carriage 14 and 15 which glides in a slide 16 at an end of the patient-supporting platform, the cranks 10, 11 being connected to the carriages 14 and 15 by rods pivots or spindles 17 which are respectively secured to their free ends.

Concentric with the common axis of the two cranks 10, 11 there is a shaft (arbor) 18 carrying a chain sprocket wheel driven by a pinion 22, which drives in rotation a double pinion 19 including two parallel sprocket wheels secured to each other and freely rotatably mounted on the spindle 17 connecting the carriage 15 to the end of the crank 11. The sprocket wheel of this double pinion 19 closest to the carriage 15, engages with and, when rotated, moves along a chain 20, suspended parallel to the slide 16, which is located at the end and parallel to the transverse axis of the platform 1. The respective ends 21 and 23 of chain 20 are respectively secured to the opposite ends of the slide 16. In this lateral transfer device of the platform 1, it is obvious to the man of the mechanical art, to replace the chain 20 and sprocket (of double pinion 19) drive by a rack and pinion-type mechanism, the toothed rack being secured along the slide 16 and parallel thereto.

Such a variant embodiment of the invention is illustrated by FIG. 3, where the sprocket of the double pinion 19 of FIG. 2 is replaced by a further pinion 25 engaging with a rack 24 secured to the slide 16.

It may be seen that the rotation of the pinion 22 drives the double pinion 19, whose rotation, by its engagement with the stationary chain 20 (or rack), controls the displacement of the slide 16, and hence the platform 1, on the carriages 14 and 15, thus ensuring the lateral displacement of the patient-supporting platform; whereas, the rotation of the pinions 12 and 13, respectively, causes the rotation of the cranks 11 and 10. Thus, it is possible to obtain the three movements described above.

Firstly, the movement of a lateral displacement of the platform 1 is obtained by turning the shaft 18 which carries the sprocket wheel 22 and which is concentric with the axes of rotation of the two cranks 10, 11 respectively materialized by means of a first and second hollow shaft respectively secured to pinions 13 and 12 and coaxial with each other and with shaft 18, as can clearly be seen from FIG. 2; when the shaft 18 turns, it drives the double pinion 19 rotatable about the spindle 17 which is mounted at the end of the crank 11. The sprocket wheel of the double pinion 19 which is located closest to the carriage 15, when rotated acts on the chain 20, fixed to the respective ends 21 and 23 of the slide 16, integral with the platform 1, and hence displaces the platform 1 parallel to the chain 20 fixed on the platform 1.

Secondly, the arcuate movement is obtained by imparting to the two cranks 10 and 11 angular speeds which are equal in absolute value and have the same sign.

Thirdly, the up-and-down movement of the platform 1, i.e. perpendicularly to the patient supporting plane it is providing, is obtained by imparting to the two cranks 10 and 11 angular speeds which are equal in absolute value but have the opposite sign.

With respect to apparatus already known, the present invention has the advantage that permits a compact emobodiment and makes it possible that the patient-supporting platform 1 can be removed to any desired distance from the motion-producing elements. Because of this fact, the access to the patient, as well as to each end of the platform 1 and each side of the platform 1, is very easy and convenient.

Furthermore, the remote control of motorizing each movement results in being able to apply each of the movements to each of the two ends of the platform 1. This produces the possibility of making a very light patient-supporting platform 1 since both of its ends are simultaneously driven either in rotation or in translation in the direction parallel to its plane or in translation in the direction perpendicular to its own plane.

Because of this fact, the patient-supporting platform can be constructed entirely of materials which are transparent to x-rays. This is a very desirable property when a mechanism is employed in a remotely controlled examination table which has a second x-ray tube whose radiation is perpendicular to the mean position of the principal x-ray tube of the scanning assembly of the remotely controlled table.

It is to be appreciated that the foregoing detailed description and accompanying figures of the drawing have been provided by way of example, not by way of limitation. Numerous other embodiments and variants are possible within the spirit and scope of the present invention, the scope being defined in the appended claims.

That which is claimed is:

1. In a radiological examination table including a patient-supporting platform having a first and a second end, a supporting mechanism for respectively supporting both said ends of said platform and for imparting thereto translational displacements, on the one hand, parallel to the transverse axis of and, on the other hand, perpendicular to the plane of said platform and rotational displacements about an axis parallel to the longitudinal axis of said platform; said supporting mechanism including a first and a second mechanism identical with each other and respectively connected to said first and second ends of said platform; each of said first and second mechanisms comprising in combination:

a slide fixed to said platform and parallel to the transverse axis thereof;

a first and a second carriage glidably mounted in said slide for displacements therealong;

a first and second pivot respectively journalled to said first and second carriages for providing two axes of rotation parallel to the longitudinal axis of said platform;

a first and a second crank having two ends and respectively carrying at one of their ends said first and second pivots, the other ends of said first and second cranks being respectively secured to a first and a second hollow shaft coaxial with each other, one of said two hollow shafts being inserted within the other one and both being independently rotatable relative to each other;

a third shaft coaxial with the common axis of said two hollow shafts and mounted independently rotatably therewithin;

a drive means, coupled to one end of said third shaft and rotatably mounted on one of said pivots, for driving a geared wheel engaging with a stationary structure substantially parallel and fixedly mounted relatively to said slide, wherein said geared wheel, when rotated, controls the displacement of said slide relative to said carriage.

2. Mechanism as claimed in claim 1, wherein said stationary structure comprises chain tensioned between the respective ends of said slide and said geared wheel comprises a sprocket engaging with said chain.

3. Mechanism as claimed in claim 1, wherein said stationary structure comprises a toothed rack mounted integrally to said slide and said geared wheel comprises a pinion engaging with the teeth of said rack.

* * * * *